(12) United States Patent
Leuenberger et al.

(10) Patent No.: US 12,227,532 B2
(45) Date of Patent: *Feb. 18, 2025

(54) CRYSTALLINE FORMS

(71) Applicant: Viatris Asia Pacific Pte. Ltd., Singapore (SG)

(72) Inventors: Daniel Leuenberger, Allschwil (CH); Stefan Reber, Allschwil (CH); Markus Von Raumer, Allschwil (CH)

(73) Assignee: Viatris Asia Pacific Ptd. Ltd., Singapore (SG)

( * ) Notice: Subject to any disclaimer, the term of this patent is extended or adjusted under 35 U.S.C. 154(b) by 353 days.

This patent is subject to a terminal disclaimer.

(21) Appl. No.: 17/741,427

(22) Filed: May 10, 2022

(65) Prior Publication Data

US 2022/0275011 A1 Sep. 1, 2022

Related U.S. Application Data

(63) Continuation of application No. 16/938,730, filed on Jul. 24, 2020, now Pat. No. 11,365,209, which is a continuation of application No. 16/335,973, filed as application No. PCT/EP2017/073858 on Sep. 21, 2017, now Pat. No. 10,730,896.

(30) Foreign Application Priority Data

Sep. 22, 2016 (WO) ............... PCT/EP2016/072562

(51) Int. Cl.
*C07F 9/6558* (2006.01)
(52) U.S. Cl.
CPC ...... *C07F 9/65583* (2013.01); *C07B 2200/13* (2013.01)

(58) Field of Classification Search
CPC .................. C07B 2200/13; C07F 9/65583
See application file for complete search history.

(56) References Cited

U.S. PATENT DOCUMENTS

| | | | |
|---|---|---|---|
| 6,855,715 B1 | 2/2005 | Liebeschuetz et al. |
| 8,044,055 B2 | 10/2011 | Caroff et al. |
| 8,048,881 B2 | 11/2011 | Caroff et al. |
| 8,058,263 B2 | 11/2011 | Caroff et al. |
| 8,067,419 B2 | 11/2011 | Binkert et al. |
| 8,093,250 B2 | 1/2012 | Caroff et al. |
| 8,288,385 B2 | 10/2012 | Caroff et al. |

(Continued)

FOREIGN PATENT DOCUMENTS

| | | |
|---|---|---|
| EP | 0407200 | 1/1991 |
| JP | S53-73586 | 6/1978 |

(Continued)

OTHER PUBLICATIONS

U.S. Appl. No. 16/938,730, filed Jul. 24, 2020, Leuenberger et al.

(Continued)

*Primary Examiner* — Savitha M Rao (57) ABSTRACT

The invention relates to crystalline forms of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester hydrochloride, processes for the preparation thereof, pharmaceutical compositions comprising said crystalline forms, pharmaceutical compositions prepared from such crystalline forms and their use as a medicament, especially as a P2Y$_{12}$ receptor antagonist.

14 Claims, 6 Drawing Sheets

(56) References Cited

U.S. PATENT DOCUMENTS

| | | |
|---|---|---|
| 8,466,156 B2 | 6/2013 | Caroff et al. |
| 8,518,912 B2 | 8/2013 | Caroff et al. |
| 8,664,203 B2 | 3/2014 | Caroff et al. |
| 10,730,896 B2 | 8/2020 | Leuenberger et al. |
| 11,365,209 B2 | 6/2022 | Leuenberger et al. |
| 2003/0060474 A1 | 3/2003 | Bryant et al. |
| 2005/0038037 A1 | 2/2005 | Bryant et al. |
| 2005/0065163 A1 | 3/2005 | Bryant et al. |
| 2021/0009614 A1 | 1/2021 | Leuenberger et al. |

FOREIGN PATENT DOCUMENTS

| | | |
|---|---|---|
| JP | A-2008-239617 | 10/2008 |
| WO | WO 2002/098856 | 12/2002 |
| WO | WO 2004/052366 | 6/2004 |
| WO | WO 2004/092189 | 10/2004 |
| WO | WO 2006/114774 | 11/2006 |
| WO | WO 2007/046075 | 4/2007 |
| WO | WO 2008/044217 | 4/2008 |
| WO | WO 2008/050301 | 5/2008 |
| WO | WO 2008/128647 | 10/2008 |
| WO | WO 2009/069100 | 6/2009 |
| WO | WO 2009/080226 | 7/2009 |
| WO | WO 2009/080227 | 7/2009 |
| WO | WO 2009/125365 | 10/2009 |
| WO | WO 2009/125366 | 10/2009 |
| WO | WO 2010/116328 | 10/2010 |
| WO | WO 2010/122504 | 10/2010 |
| WO | WO 2018/167139 | 9/2018 |
| WO | WO 2022/013276 | 1/2022 |

OTHER PUBLICATIONS

Abele, S., "Pilot Plant Production of a $P2Y_{12}$-Antagonist Containing (R)-3-Phosphonoalanine," $250^{th}$ ACS National Meeting & Exposition, Boston, MA, United States, Aug. 16-20, 2015, ORGN-229, Abstract, 1 page.

Abele, S., "Pilot Plant Production of a $P2Y_{12}$-Antagonist Containing (R)-3-Phosphonoalanine," $250^{th}$ ACS National Meeting & Exposition, Boston, MA, United States, Aug. 17, 2015, 51 pages.

Amir, J., et al., "Treatment of Thrombotic Thrombocytopeniarpura With Antiplatelet Drugs," Blood, 1973, 42(1):27-33.

Antithrombotic Trialists' Collaboration, "Collaborative meta-analysis of randomised trials of antiplatelet therapy for prevention of death, myocardial infarction, and stroke in high risk patients," British Medical Journal, 2002, 324:71-86.

Baldoni, D., et al., "A New Reversible and Potent $P2Y_{12}$ Receptor Antagonist (ACT-246475): Tolerability, Pharmacokinetics, and Pharmacodynamics in a First-in-Man Trial," Clinical Drug Investigation, 2014, 34(11):807-818.

Balduini, C., et al., "Platelet Aggregation in Platelet-Rich Plasma and Whole Blood in 120 Patients with Myeloproliferative Disorders," Coagulation and Transfusion Medicine, 1991, 95(1):82-86.

Bartoli, G., et al., "Reaction of Dianions of Acyclic Beta-Enamino Ketones with Electrophiles. 3. Nitriles: Synthesis of Pyridine and Pyrimidine Derivatives," J. Org. Chem., 1992, 57:6020-6025.

Belanger, G., et al., "New Approach to Aphidicolin and Total Asymmetric Synthesis of Unnatural (11R)-(−)-8-Epi-11-hydroxyaphidicolin by Tandem Transannular Diels-Alder/Aldol Reactions," J. Org. Chem., 2000, 65:7070-7074.

Berge, et al., "Pharmaceutical Salts," J. Pharm. Sci., vol. 66, No. 1, pp. 1-19 (1977).

Bertrand, M.E., et al., "Randomized Multicenter Comparison of Conventional Anticoagulation Versus Antiplatelet Therapy in Unplanned and Elective Coronary Stenting," Circulation, 1998, 98:1597-1603.

Brighton, T.A., et al., "Antiphospholipid antibodies and thrombosis," Bailliere's Clinical Haematology, 1994, 7(3): 541-557.

Caira, et al., "Crystalline Polymorphism of Organic Compounds," Topics in Current Chemistry, vol. 198, pp. 163-208 (1998).

CAPRIE Steering Committee, "A randomised, blinded, trial of clopidogrel versus aspirin in patients at risk of ischaemic events (CAPRIE)," The Lancet, 1996, 248:1329-1339.

Caroff, E., et al., "Optimization of 2-phenyl-pyrimidine-4-carboxamides towards potent, orally bioavailable and selective $P2Y_{12}$ antagonists for inhibition of platelet aggregation," Bioorganic & Medicinal Chemistry Letters, 2014, 24(17):4323-4331.

Caroff, E., et al., "4-((R)-2-{[6-((S)-3-Methoxypyrrolidin-1-yl)-2-phenylpyrimidine-4-carbonyl]amino}-3-phosphonopropionyl)piperazine-1-carboxylic Acid Butyl Ester (ACT-246475) and Its Prodrug (ACT-281959), a Novel $P2Y_{12}$ Receptor Antagonist with a Wider Therapeutic Window in the Rat Than Clopidogrel," J. Med. Chem., 2015, 58(23):9133-9153.

Cattaneo, M., et al., "The platelet $P2Y_{12}$ receptor for adenosine diphosphate: congenital and drug-induced defects," Blood, 2011, 117(7):2102-2112.

Charette, A.B., et al., "Enantioselective Cyclopropanation of Allylic Alcohols with Dioxaborolane Ligands: Scope and Synthetic Applications," J. Am. Chem., 1998, 120:11943-11952.

ClinicalTrials.gov, ClinicalTrials.gov Identifier: NCT00222677, "Aspirin for the Prevention of Recurrent Venous Thromboembolism," University of Perugia, Sep. 22, 2005, 6 pages.

ClinicalTrials.gov, ClinicalTrials.gov Identifier: NCT01954615, "Single-ascending Oral Dose Study to Investigate the Safety, Tolerability, Pharmacokinetics, and Pharmacodynamics of ACT-281959 / ACT-246475 in Healthy Male Subjects," Oct. 7, 2013, 8 pages.

ClinicalTrials.gov, ClinicalTrials.gov Identifier: NCT03384966, "A Medical Research Study to Evaluate the Effects of ACT-246475 in Adults with Coronary Artery Disease," Dec. 28, 2017, 6 pages.

ClinicalTrials.gov, ClinicalTrials.gov Identifier: NCT03430661, "A Study to Investigate the Interaction Between ACT-246475 and Clopidogrel, Prasugrel, and Ticagrelor in Healthy Subjects," Feb. 13, 2018, 8 pages.

ClinicalTrials.gov, ClinicalTrials.gov Identifier: NCT03487445, "A Medical Research Study to Evaluate the Effects of ACT-246475 in Adults with Heart Attack," Apr. 4, 2018, 4 pages.

ClinicalTrials.gov, ClinicalTrials.gov Identifier: NCT03593278, "A Study to Evaluate ACT-246475 Fate in Healthy Male Subjects," Jul. 20, 2018, 5 pages.

ClinicalTrials.gov, ClinicalTrials.gov Identifier: NCT03814200, "A Study to Investigate the Effect of Rifampicin on the Uptake and Breakdown of ACT-246475 in Healthy Subjects," Jan. 23, 2019, 5 pages.

Coller, B.S., et al., "Historical Perspective and Future Directions in Platelet Research," J Thromb Haemost., 2011, 9 (Suppl. 1):374-395.

Collins, C.E., et al., "Review article: platelets in inflammatory bowel disease—pathogenetic role and therapeutic implications," Aliment Pharmacol. Ther., 1997, 11:237-247.

Davies et al. "Intramyocardial platelet aggregation in patients with unstable angina suffering sudden ischemic cardiac death." Circulation, 1986, 73(3):418-427.

Felfernig-Boehm et al., "Early Detection of Preeclampsia by Determination of Platelet Aggregability," Thrombosis Research, 2000, 98:139-146.

Feokistov et al., "Adenosine $A_{2B}$ Receptors," Pharmaceutical Reviews, 1997, 49(4):381-402.

Fox et al., "Benefits and Risks of the Combination of Clopidogrel and Aspirin in Patients Undergoing Surgical Revascularization for Non-ST-Elevation Acute Coronary Syndrome," Circulation, 2004, 110:1202-1208.

Halushka et al., "Protective Effects of Aspirin in Endotoxic Shock," The Journal of Pharmacology and Experimental Therapeutics, 1981, 218(2):464-469.

Hilfiker et al., "Polymorphism in the Pharmaceutical Industry, Chapter 8: U.J. Griesser: The Importance of Solvates." 2006, 19 pages.

Hovens et al., "Aspirin in the prevention and treatment of venous thromboembolism," Journal of Thrombosis and Haemostasis, 2006, 4:1470-1475.

International Search Report for International Application No. PCT/EP2017/073858, prepared by the International Searching Authority, Date Mailed: Oct. 18, 2017, 4 pages.

(56) References Cited

OTHER PUBLICATIONS

Jagroop, I.A., et al., "The effect of clopidogrel, aspirin and both antiplatelet drugs on platelet function in patients with peripheral arterial disease," Platelets, 2004, 15:117-125.

Jneid, H., et al., "2012 ACCF/AHA Focused Update of the Guideline for the Management of Patients with Unstable Angina/Non-ST-Elevation Myocardial Infarction (Updating the 2007 Guideline and Replacing the 2011 Focused Update)," J Am Coll Cardiol., 2012, 60(7):645-681.

Kharbanda et al., "Prevention of Inflammation-Induced Endothelial Dysfunction—A Novel Vasculo-Protective Action of Aspirin," Circulation, 2002, 105:2600-2604.

Liu et al., "$P2Y_{12}$ receptor inhibitors for secondary prevention of ischemic stroke," Expert Opinion on Pharmacotherapy, 2015, 16(8):1149-1165.

Matsagas, M., et al., "The Effect of a Loading Dose (300 mg) of Clopidogrel on Platelet Function in Patients with Peripheral Arterial Disease," Clin Appl Thromb Hemost., 2003, 9:115-120.

Megalopoulos, A., et al., "Recurrent arterial thromboses in a woman with heparin induced thrombocytopenia, successfully managed with iloprost followed by clopidogrel. An alternative therapeutic option for heparin induced thrombocytopenia type II syndrome," International Angiology, 2006, 25(1):84-89.

Mehta et al., "Effects of pretreatment with clopidogrel and aspirin followed by long-term therapy in patients undergoing percutaneous coronary intervention: the PCI-CURE study," The Lancet, 2001, 358:527-533.

Norgard, N., "Cangrelor: a novel P2Y12 receptor antagonist," Expert Opinion on Investigational Drugs, 2009, 18(8):1219-1230.

Notice of Allowance dated Jun. 27, 2011, for U.S. Appl. No. 12/936,661.

Office Action dated Aug. 31, 2012, for U.S. Appl. No. 12/936,664.
Office Action dated Jan. 21, 2011, for U.S. Appl. No. 12/936,661.
Office Action dated Jan. 19, 2011, for U.S. Appl. No. 12/445,352.
Office Action dated Oct. 28, 2010, for U.S. Appl. No. 11/912,545.

O'Gara, P.T., "2013 ACCF/AHA Guideline for the Management of ST-Elevation Myocardial Infarction," Circulation, 2013, 127:e362-425.

Parlow, J.J., et al., "Piperazinyl Glutamate Pyridines as Potent Orally Bioavailable $P2Y_{12}$ Antagonists for Inhibition of Platelet Aggregation," J.Med. Chem., 2010, 53:2010-2037.

Parlow, J.J., et al., "Piperazinyl-glutamate-pyridines as Potent Orally Bioavailable $P2Y_{12}$ Antagonists for Inhibition of Platelet Aggregation," Bioorg. Med. Chem. Lett., 2009, 19:4657-4663.

Parlow, J.J., et al., "Piperazinyl-glutamate-pyridines as Potent Orally Bioavailable $P2Y_{12}$ Antagonists for Inhibition of Platelet Aggregation," Bioorg. Med. Chem. Lett., 2009, 19:6148-6156.

Payne et al., "Beneficial Effects of Clopidogrel Combined with Aspirin in Reducing Cerebral Emboli in Patients Undergoing Carotid Endarterectomy," Circulation 2004, 109:1476-1481.

Remington, The Science and Practice of Pharmacy, $21^{st}$ Edition, 2005, Part 5, Pharmaceutical Manufacturing, 5 pages.

Rey, M., et al., "The reversible $P2Y_{12}$ antagonist ACT-246475 causes significantly less blood loss than ticagrelor at equivalent antithrombotic efficacy in rat," Pharmacology Research & Perspective, 2017, 5:e0033, pp. 1-11.

Shao et al., "Phenoxyphenyl Pyridines as Novel State-Dependent, High-Potency Sodium Channel Inhibitors," J. Med. Chem., 2004, 47:4277-4285.

Sheppard et al., Discovery and Optimization of Anthranilic Acid Sulfonamides as Inhibitors of Methionine Aminopeptidase-2: A Structural Basis for the Reduction of Albumin Binding, 2006, 49:3832-3849.

Stahl, H., C.G. Wermuth Handboook of Pharmaceutical Salts. Properties, Selection and Use, 2008, 22 pages.

Stathakis et al., "Platelet Dysfunction in Essential Thrombocythaemia," Annals of Clinical Research, 1974, 6:198-202.

Thomas, M.R., et al., "The future of $P2Y_{12}$ receptor antagonists," Platelets, 2015, 26:392-398.

Thorsen, C.A., et al., "The Treatment of the Hemolytic-Uremic Syndrome with Inhibitors of Platelet Function," The American Journal of Medicine, 1979, 66:711-716.

Triadou et al., "Platelet function in sickle cell disease during steady state," Nouvelle Revue Francaise Hematologie, 1990, 32:137-142.

Wallentin, L., et al., "$P2Y_{12}$ inhibitors: differences in properties and mechanisms of action and potential consequences for clinical use," European Heart Journal, 2009, 30:1964-1977.

Wiviott, S.D., et al., "Novel antithrombotic agents 2—Clinical evidence for oral antiplatelet therapy in acute coronary syndromes," Lancet, 2015, 386:292-302.

Johan Wouters and Luc Quéré, "Pharmaceutical Salts and Co-crystals," RSC Drug Discovery, 2012, Series No. 16, pp. vii-xiv.

Yao et al., "Clopidogrel is more effective than aspirin as adjuvant treatment to prevent reocclusion after thrombolysis," Am. J. Physiol., 1994, 267:H488-H493.

U.S. Appl. No. 18/016,299, Jan. 13, 2023 (371(c) Date), Buchmann et al.

CRYSTALLINE FORMS

CROSS REFERENCE TO RELATED APPLICATIONS

This application is a continuation of U.S. patent application Ser. No. 16/938,730 filed Jul. 24, 2020, which is a continuation of U.S. patent application Ser. No. 16/335,973 filed Mar. 22, 2019, now issued as U.S. Pat. No. 10,730,896, which is a United States Application under 37 U.S.C. 371 claiming benefit of PCT Application No. PCT/EP2017/073858, filed on Sep. 21, 2017, which claims the benefit of PCT Application No. PCT/EP2016/072562, filed on Sep. 22, 2016, the contents of each of which are incorporated herein by reference.

The invention relates to novel crystalline forms of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester hydrochloride (hereinafter also referred to as "COMPOUND·HCl"), processes for the preparation thereof, pharmaceutical compositions comprising said crystalline forms, pharmaceutical compositions comprising 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester (hereinafter also referred to as "COMPOUND") wherein COMPOUND is obtained from said crystalline forms of COMPOUND·HCl, pharmaceutical compositions prepared from such crystalline forms of COMPOUND·HCl, use of the crystalline forms of COMPOUND·HCl as $P2Y_{12}$ receptor antagonists in the treatment of various $P2Y_{12}$ receptor-mediated diseases and disorders and use of COMPOUND as $P2Y_{12}$ receptor antagonist in the treatment of various $P2Y_{12}$ receptor-mediated diseases and disorders wherein COMPOUND is obtained from said crystalline forms of COMPOUND·HCl.

BACKGROUND OF THE INVENTION

The circulation of blood from and to organs guarantees the supply of oxygen, nutrients, as well as the disposal of catabolic products. Therefore, the integrity of blood vessels is essential at all times. When the vascular integrity is compromised, a highly efficient repair mechanism is activated at the site of injury resulting in the formation of a repair seal to prevent further blood loss. This fundamental biological process is defined as hemostasis. Thrombosis is the result of a pathological deviation of one or several components involved in hemostasis leading to uncontrolled platelet thrombus formation and vessel occlusion. Platelets have been described to contribute to hemostasis and thrombosis since their discovery (Coller B S, Historical perspective and future directions in platelet research. *J Thromb Haemost.* 2011; 9 Suppl 1:374-395). More recently, atherosclerotic lesions in combination with occlusive platelet thrombi have been found in patients with ischemic cardiac death (Davies M J et al., Intramyocardial platelet aggregation in patients with unstable angina suffering sudden ischemic cardiac death. *Circulation.* 1986; 73:418-427).

Inhibition of platelet aggregation is recognized as an effective strategy for the prevention of thrombosis in patients with atherosclerotic disease in the coronary (Jneid H et al., 2012 accf/aha focused update of the guideline for the management of patients with unstable angina/non-st-elevation myocardial infarction (updating the 2007 guideline and replacing the 2011 focused update): A report of the american college of cardiology foundation/american heart association task force on practice guidelines. *J Am Coll Cardiol.* 2012; 60:645-681; O'Gara P T et al., 2013 accf/aha guideline for the management of st-elevation myocardial infarction: A report of the american college of cardiology foundation/american heart association task force on practice guidelines. *Circulation.* 2013; 127:e362-425), peripheral (Jagroop I A et al., The effect of clopidogrel, aspirin and both antiplatelet drugs on platelet function in patients with peripheral arterial disease. *Platelets.* 2004; 15:117-125; Matsagas M et al., The effect of a loading dose (300 mg) of clopidogrel on platelet function in patients with peripheral arterial disease. *Clin Appl Thromb Hemost.* 2003; 9:115-120), and cerebrovascular circulation (Liu F et al., $P2Y_{12}$ receptor inhibitors for secondary prevention of ischemic stroke. *Expert Opin Pharmacother.* 2015; 16:1149-1165). Inhibition of $P2Y_{12}$ as an antiplatelet approach was validated in multiple clinical studies. Several $P2Y_{12}$ antagonists have been demonstrated to effectively reduce the risk of adverse cardiovascular events in patients with acute coronary syndromes (ACS) and patients undergoing percutaneous coronary intervention (PCI) (Cattaneo M, The platelet $P2Y_{12}$ receptor for adenosine diphosphate: Congenital and drug-induced defects. *Blood.* 2011; 117:2102-2112; Thomas M R et al., The future of $P2Y_{12}$ receptor antagonists. *Platelets.* 2015; 26:392-398; Wiviott S D et al., Clinical evidence for oral antiplatelet therapy in acute coronary syndromes. *Lancet.* 2015; 386: 292-302; Wallentin L, $P2Y_{12}$ inhibitors: Differences in properties and mechanisms of action and potential consequences for clinical use. *Eur Heart J.* 2009; 30:1964-1977). In current treatment guidelines, $P2Y_{12}$ antagonists define the cornerstone therapy for patients with ACS (Jneid H et al., 2012 accf/aha focused update of the guideline for the management of patients with unstable angina/non-st-elevation myocardial infarction (updating the 2007 guideline and replacing the 2011 focused update): A report of the american college of cardiology foundation/american heart association task force on practice guidelines. *J Am Coll Cardiol.* 2012; 60:645-681; O'Gara P T et al., 2013 accf/aha guideline for the management of st-elevation myocardial infarction: A report of the american college of cardiology foundation/american heart association task force on practice guidelines. Circulation. 2013; 127:e362-425).

Three indirect $P2Y_{12}$ antagonists of the thienopyridine family, which block the ADP-induced platelet activation and aggregation, have reached the market: the orally active ticlopidine, clopidogrel and prasugrel. In addition, two direct $P2Y_{12}$ antagonists, which do not require metabolic activation and therefore display faster on- and offset of action, have received market approval: the nucleotide analogues ticagrelor and cangrelor. 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester is a potent, reversible, and selective $P2Y_{12}$ receptor antagonist (Caroff E et al., *J. Med. Chem.* 2015; 58:9133-9153; WO 2009/069100). Its hydrochloride salt was used as a powder in a first-in-man clinical trial (Baldoni et al., *Clinical Drug Investigation* 2014; 34:807-818).

Despite the fact that many attempts failed to crystallize COMPOUND·HCl from several solvents in a mono-phase solvent system, it surprisingly has been found that a crystallization took place in certain heterogeneous solvent systems. The obtained crystalline forms of COMPOUND·HCl may have advantageous properties in view of the potential use of COMPOUND·HCl or COMPOUND as active pharmaceutical ingredient. Such advantages may include higher purity; better storage stability; better flow properties; less hygroscopicity; better reproducibility in manufacturing (for example better filtration parameters, better reproducibility of formation, and/or better sedimentation); and/or defined morphology. Such crystalline forms of COMPOUND·HCl may be particularly suitable in a process of manufacturing certain pharmaceutical compositions.

DESCRIPTION OF THE FIGURES

In the X-ray diffraction diagrams of FIG. 1 to FIG. 3 the angle of refraction 2theta (2θ) is plotted on the horizontal axis and the counts on the vertical axis.

For avoidance of any doubt, the above-listed peaks describe the experimental results of the X-ray powder diffraction shown in FIGS. 1 to 3. It is understood that, in contrast to the above peak list, only a selection of characteristic peaks is required to fully and unambiguously characterize COMPOUND·HCl in the respective crystalline form of the present invention.

In the gravimetric vapour sorption diagrams of FIGS. 4, 5, and 6 the relative humidity (% RH) is plotted on the horizontal axis and the mass change (% dm, dry basis) on the vertical axis.

DETAILED DESCRIPTION OF THE INVENTION

1) A first embodiment of the invention relates to crystalline forms of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester hydrochloride (COMPOUND·HCl), characterized by:
   a. the presence of peaks in the X-ray powder diffraction diagram at the following angles of refraction 2θ: 4.0°, 5.0°, and 15.3° (form 1); or
   b. the presence of peaks in the X-ray powder diffraction diagram at the following angles of refraction 2θ: 5.2°, 6.8°, and 10.3° (form 2); or
   c. the presence of peaks in the X-ray powder diffraction diagram at the following angles of refraction 2θ: 5.5°, 11.0°, and 16.6° (form 3).

It is understood, that the crystalline forms according to embodiment 1) comprise COMPOUND·HCl in form of the hydrochloric acid (hydrochloride) salt. Furthermore, said crystalline form may comprise non-coordinated and/or coordinated solvent (especially non-coordinated and/or coordinated water). Coordinated solvent (especially coordinated water) is used herein as term for a crystalline solvate (especially a crystalline hydrate). For the avoidance of doubt, in this application the term "crystalline hydrate" encompasses non-stoichiometric hydrates. Likewise, non-coordinated solvent is used herein as term for physiosorbed or physically entrapped solvent (definitions according to Polymorphism in the Pharmaceutical Industry (Ed. R. Hilfiker, V C H, 2006), Chapter 8: U. J. Griesser: The Importance of Solvates). It is further understood, that the crystalline form may contain different amounts of coordinated water as a function of relative humidity and that the X-ray powder diffraction diagram may thus vary with relative humidity. Crystalline form 1 in particular comprises about 0 to 3% of coordinated and/or non-coordinated water. Cystalline form 2 in particular comprises about 5 to 10% of coordinated and/or non-coordinated water. Crystalline form 3 in particular comprises about 2.5 to 8% of coordinated and/or non-coordinated water.

2) Another embodiment relates to crystalline forms of COMPOUND·HCl according to embodiment 1), characterized by
   a. the presence of peaks in the X-ray powder diffraction diagram at the following angles of refraction 2θ: 4.0°, 5.0°, 11.7°, 15.3°, and 19.3° (form 1); or
   b. the presence of peaks in the X-ray powder diffraction diagram at the following angles of refraction 2θ: 5.2°, 6.8°, 10.3°, 10.8°, and 15.4° (form 2); or
   c. the presence of peaks in the X-ray powder diffraction diagram at the following angles of refraction 2θ: 5.5°, 7.2°, 11.0°, 11.5°, and 16.6° (form 3).

3) Another embodiment relates to crystalline forms of COMPOUND·HCl according to embodiment 1), characterized by a. the presence of peaks in the X-ray powder diffraction diagram at the following angles of refraction 2θ: 4.0°, 5.0°, 5.9°, 11.7°, 15.3°, 16.9°, 19.3°, 19.7°, and 20.7° (form 1); or b. the presence of peaks in the X-ray powder diffraction diagram at the following angles of refraction 2θ: 5.2°, 6.8°, 8.0°, 10.3°, 10.8°, 12.7°, 15.4°, 16.2°, 20.3°, and 21.7° (form 2); or c. the presence of peaks in the X-ray powder diffraction diagram at the following angles of refraction 2θ: 5.5°, 7.2°, 11.0°, 11.5°, 14.4°, 16.6°, 18.1°, 21.1°, and 22.0° (form 3).

4) Another embodiment relates to a crystalline form of COMPOUND·HCl according to embodiment 1), characterized by the presence of peaks in the X-ray powder diffraction diagram at the following angles of refraction 2θ: 4.0°, 5.0°, and 15.3°.

5) Another embodiment relates to a crystalline form of COMPOUND·HCl according to embodiment 1), characterized by the presence of peaks in the X-ray powder diffraction diagram at the following angles of refraction 2θ: 4.0°, 5.0°, 11.7°, 15.3°, and 19.3°.

6) Another embodiment relates to a crystalline form of COMPOUND·HCl according to embodiment 1), characterized by the presence of peaks in the X-ray powder diffraction diagram at the following angles of refraction 2θ: 4.0°, 5.0°, 5.9°, 11.7°, 15.3°, 16.9°, 19.3°, 19.7°, and 20.7°.

Figure 1:
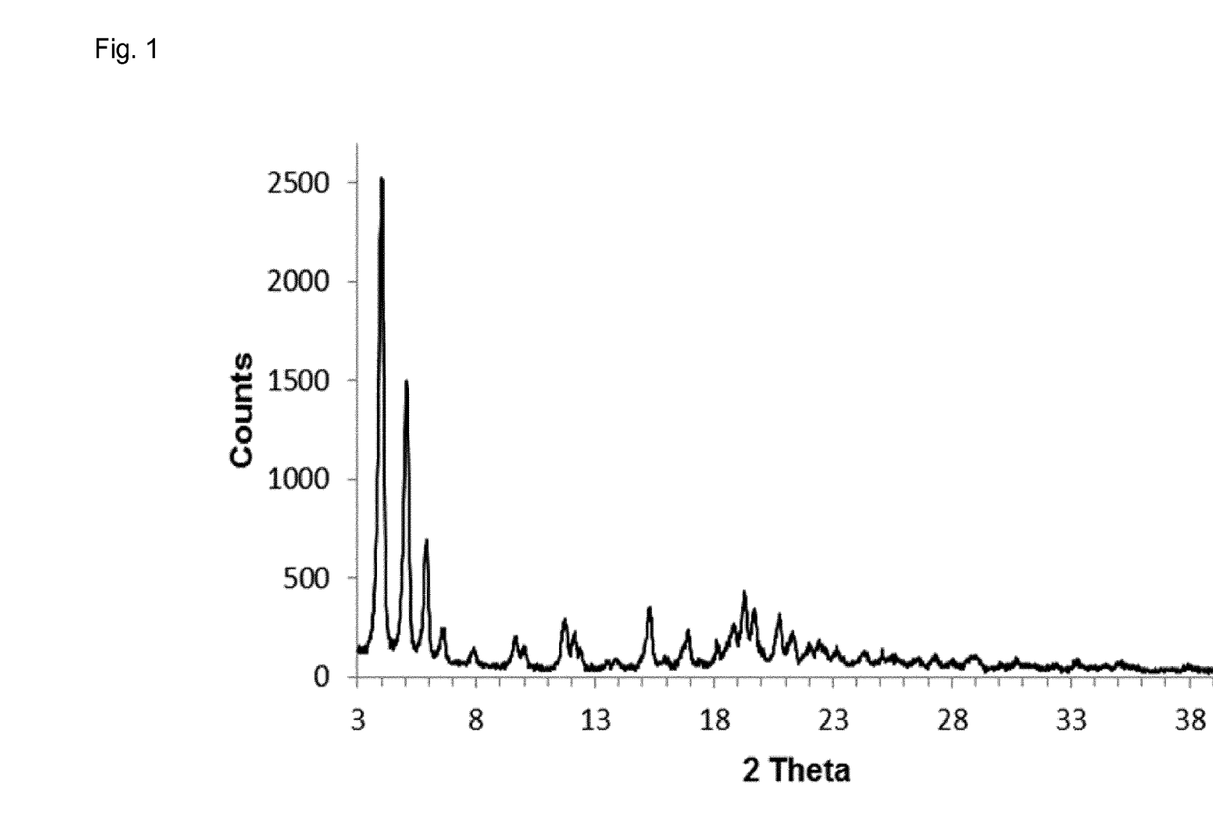
FIG. 1 shows the X-ray powder diffraction diagram of COMPOUND·HCl in the crystalline form 1, wherein the X-ray powder diffraction diagram is displayed against Cu Kα radiation. The X-ray diffraction diagram shows peaks having a relative intensity, as compared to the most intense peak in the diagram, of the following percentages (relative peak intensities given in parenthesis) at the indicated angles of refraction 2theta (selected peaks from the range 3-30° 2theta with relative intensity larger or equal than 10% are reported): 4.0° (100%), 5.0 (60%), 5.9° (23%), 11.7° (10%), 15.3° (13%), 19.3° (15%), 19.7° (11%), and 20.7° (10%).

7) Another embodiment relates to a crystalline form of COMPOUND·HCl according to embodiment 1), which essentially shows the X-ray powder diffraction pattern as depicted in FIG. 1.

8) Another embodiment relates to a crystalline form of COMPOUND·HCl according to embodiment 1), characterized by the presence of peaks in the X-ray powder diffraction diagram at the following angles of refraction 2θ: 5.2°, 6.8°, and 10.3°.

9) Another embodiment relates to a crystalline form of COMPOUND·HCl according to embodiment 1), characterized by the presence of peaks in the X-ray powder diffraction diagram at the following angles of refraction 2θ: 5.2°, 6.8°, 10.3°, 10.8°, and 15.4°.

10) Another embodiment relates to a crystalline form of COMPOUND·HCl according to embodiment 1), characterized by the presence of peaks in the X-ray powder diffraction diagram at the following angles of refraction 2θ: 5.2°, 6.8°, 8.0°, 10.3°, 10.8°, 12.7°, 15.4°, 16.2°, 20.3°, and 21.7°.

Figure 2:
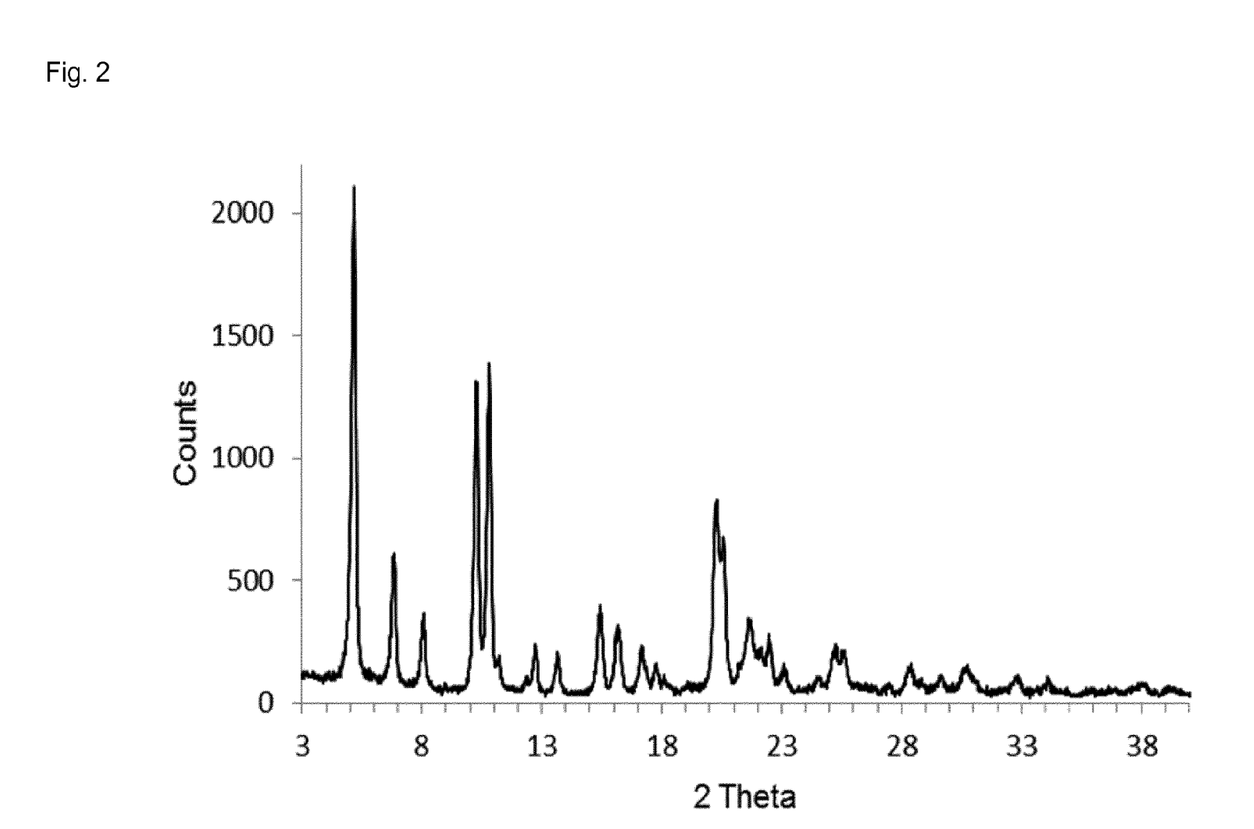
FIG. 2 shows the X-ray powder diffraction diagram of COMPOUND·HCl in the crystalline form 2, wherein the X-ray powder diffraction diagram is displayed against Cu Kα radiation. The X-ray diffraction diagram shows peaks having a relative intensity, as compared to the most intense peak in the diagram, of the following percentages (relative peak intensities given in parenthesis) at the indicated angles of refraction 2theta (selected peaks from the range 3-30° 2theta with relative intensity larger or equal than 10% are reported): 5.2° (100%), 6.8° (26%), 8.0° (14%), 10.3° (66%), 10.8° (66%), 12.7° (10%), 15.4° (18%), 16.2° (13%), 20.3° (40%), 20.5° (28%), and 21.7° (13%).

11) Another embodiment relates to a crystalline form of COMPOUND·HCl according to embodiment 1), which essentially shows the X-ray powder diffraction pattern as depicted in FIG. 2.

12) Another embodiment relates to a crystalline form of COMPOUND·HCl according to embodiment 1), characterized by the presence of peaks in the X-ray powder diffraction diagram at the following angles of refraction 2θ: 5.5°, 11.0°, and 16.6°.

13) Another embodiment relates to a crystalline form of COMPOUND·HCl according to embodiment 1), characterized by the presence of peaks in the X-ray powder diffraction diagram at the following angles of refraction 2θ: 5.5°, 7.2°, 11.0°, 11.5°, and 16.6°.

14) Another embodiment relates to a crystalline form of COMPOUND·HCl according to embodiment 1), characterized by the presence of peaks in the X-ray powder diffraction diagram at the following angles of refraction 2θ: 5.5°, 7.2°, 11.0°, 11.5°, 14.4°, 16.6°, 18.10, 21.1°, and 22.0°.

Figure 3:
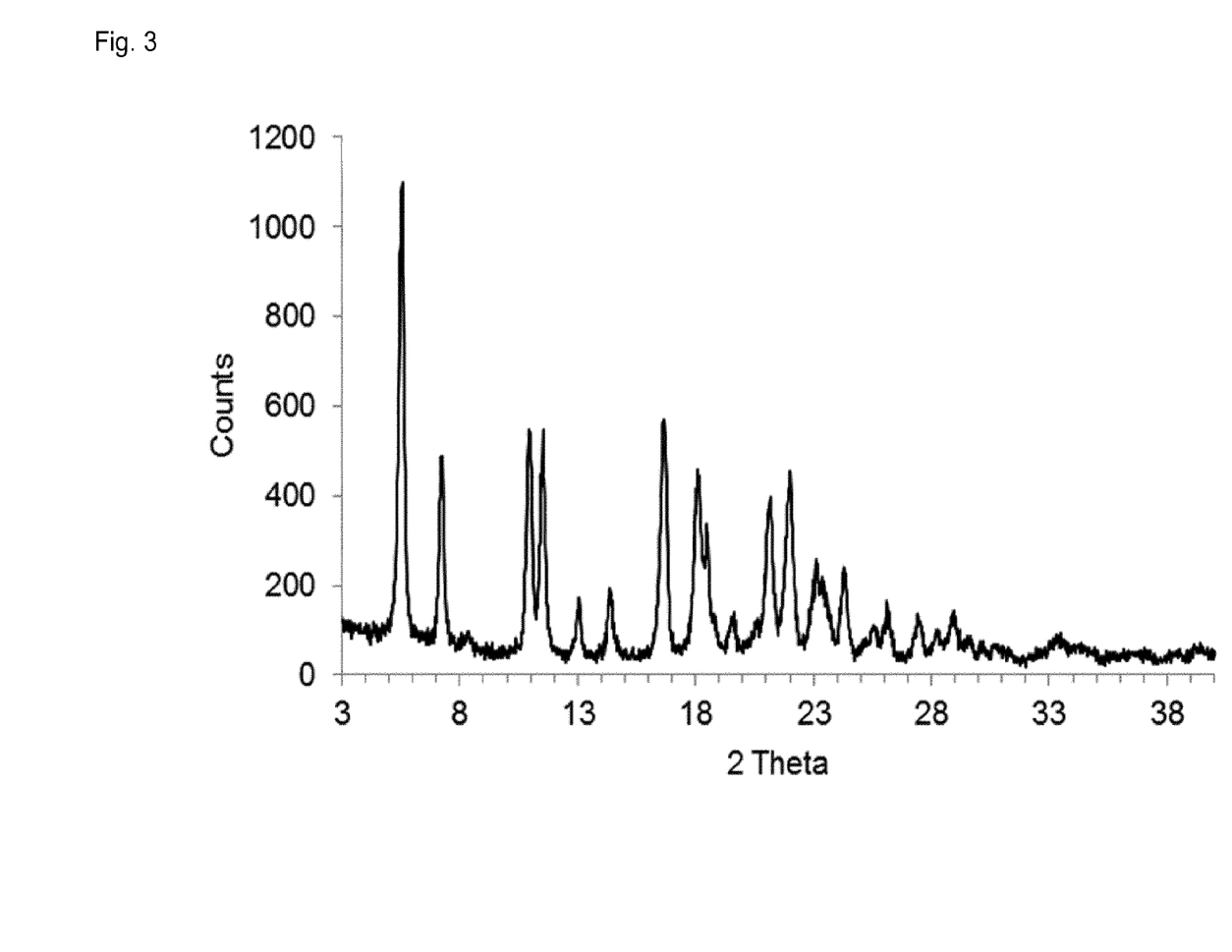
FIG. 3 shows the X-ray powder diffraction diagram of COMPOUND·HCl in the crystalline form 3, wherein the X-ray powder diffraction diagram is displayed against Cu Kα radiation. The X-ray diffraction diagram shows peaks having a relative intensity, as compared to the most intense peak in the diagram, of the following percentages (relative peak intensities given in parenthesis) at the indicated angles of refraction 2theta (selected peaks from the range 8-30° 2theta with relative intensity larger or equal than 10% are reported): 5.5° (100%), 7.2 (43%), 11.0° (51%), 11.5° (45%), 13.0° (10%), 14.4° (15%), 16.6° (51%), 18.1° (39%), 18.5° (27%), 21.10 (32%), 22.0° (37%), 23.10 (17%), 24.3° (16%) and 26.1° (10%).

15) Another embodiment relates to a crystalline form of COMPOUND·HCl according to embodiment 1), which essentially shows the X-ray powder diffraction pattern as depicted in FIG. 3.

16) Another embodiment relates to a crystalline form, such as an essentially pure crystalline form, of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester hydrochloride (COMPOUND·HCl) obtainable by:

a. addition of aq. 33% HCl (5.1 vol.) to a solution of butyl 4-((R)-3-(diethoxyphosphoryl)-2-(6-((S)-3-methoxypyrrolidin-1-yl)-2-phenylpyrimidine-4-carboxamido)propanoyl)piperazine-1-carboxylate in a mixture of DCM and THF (5.5 vol.);

b. stirring for 4 to 12 h at a temperature of 20 to 30° C.;

c. addition of water (8.2 vol.) and DCM (8.2 vol.) at a temperature of 20 to 30° C.;

d. separation of layers and extraction with DCM (8.2 vol.);

e. removal of solvent by distillation at $T_i$=50° C., addition of acetone (8.7 vol.) and further removal of solvent by distillation at $T_i$=50° C. until a final amount of 7.0 vol. remains;

f. addition of acetone (18.5 vol.) at $T_i$=50° C.;

g. addition of water (0.5 vol.) at $T_i$=50° C. within 30 min and stirring at $T_i$=56° C. for 3.5 h;

h. cooling to 20 to 30° C. within 2 h and stirring at 20 to 30° C. for 1.5 h; and i. isolation of the obtained solid residue.

17) Another embodiment relates to a crystalline form of COMPOUND·HCl according to embodiment 16), characterized by the presence of peaks in the X-ray powder diffraction diagram at the following angles of refraction 2θ: 4.0°, 5.0°, and 15.3°.

18) Another embodiment relates to a crystalline form of COMPOUND·HCl according to embodiment 16), characterized by the presence of peaks in the X-ray powder diffraction diagram at the following angles of refraction 2θ: 4.0°, 5.0°, 11.7°, 15.3°, and 19.3°.

19) Another embodiment relates to a crystalline form of COMPOUND·HCl according to embodiment 16), characterized by the presence of peaks in the X-ray powder diffraction diagram at the following angles of refraction 2θ: 4.0°, 5.0°, 5.9°, 11.7°, 15.3°, 16.9°, 19.3°, 19.7°, and 20.7°.

20) Another embodiment relates to a crystalline form of COMPOUND·HCl according to embodiment 16), which essentially shows the X-ray powder diffraction pattern as depicted in FIG. 1.

21) Another embodiment relates to the crystalline form of COMPOUND·HCl according to any one of embodiments 4) to 7), obtainable by the process of embodiment 16).

22) Another embodiment relates to a crystalline form, such as an essentially pure crystalline form, of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester hydrochloride (COMPOUND·HCl) obtainable by:

a) equilibration of a sample of COMPOUND·HCl in a crystalline form according to any one of embodiments 4) to 7) at RH>90% and at about RT; and b) equilibration of the obtained sample at about RH=40% and at about RT.

Especially, the first equilibration step requires about 3 days and the second equilibration step requires about 1 day.

23) Another embodiment relates to a crystalline form of COMPOUND·HCl according to embodiment 22), characterized by the presence of peaks in the X-ray powder diffraction diagram at the following angles of refraction 2θ: 5.2°, 6.8°, and 10.3°.

24) Another embodiment relates to a crystalline form of COMPOUND·HCl according to embodiment 22), characterized by the presence of peaks in the X-ray powder diffraction diagram at the following angles of refraction 2θ: 5.2°, 6.8°, 10.3°, 10.8°, and 15.4°.

25) Another embodiment relates to a crystalline form of COMPOUND·HCl according to embodiment 22), characterized by the presence of peaks in the X-ray powder diffraction diagram at the following angles of refraction 2θ: 5.2°, 6.8°, 8.0°, 10.3°, 10.8°, 12.7°, 15.4°, 16.2°, 20.3°, and 21.7°. 26) Another embodiment relates to a crystalline form of COMPOUND·HCl according to embodiment 22), which essentially shows the X-ray powder diffraction pattern as depicted in FIG. 2.

27) Another embodiment relates to the crystalline form of COMPOUND·HCl according to any one of embodiments 8) to 11), obtainable by the processes of embodiment 22).

28) Another embodiment relates to a crystalline form, such as an essentially pure crystalline form, of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester hydrochloride (COMPOUND·HCl) obtainable by:

a) equilibration of a sample of COMPOUND·HCl in a crystalline form according to any one of embodiments 8) to 11) in a dry nitrogen gas stream at about RT; and b) equilibration of the obtained sample at about RH=40% and at about RT.

Especially, the first equilibration step requires about 1 day for a 100 mg sample at a gas stream of about 400 mL/min and the second equilibration step requires about 1 day.

29) Another embodiment relates to a crystalline form of COMPOUND·HCl according to embodiment 28), characterized by the presence of peaks in the X-ray powder diffraction diagram at the following angles of refraction 2θ: 5.5°, 11.0°, and 16.6°.

30) Another embodiment relates to a crystalline form of COMPOUND·HCl according to embodiment 28), characterized by the presence of peaks in the X-ray powder diffraction diagram at the following angles of refraction 2θ: 5.5°, 7.2°, 11.0°, 11.5°, and 16.6°.

31) Another embodiment relates to a crystalline form of COMPOUND·HCl according to embodiment 28), characterized by the presence of peaks in the X-ray powder diffraction diagram at the following angles of refraction 2θ: 5.5°, 7.2°, 11.0°, 11.5°, 14.4°, 16.6°, 18.1°, 21.1°, and 22.0°.

32) Another embodiment relates to a crystalline form of COMPOUND·HCl according to embodiment 28), which essentially shows the X-ray powder diffraction pattern as depicted in FIG. 3.

33) Another embodiment relates to the crystalline form of COMPOUND·HCl according to any one of embodiments 12) to 15), obtainable by the processes of embodiment 28).

Figure 4:
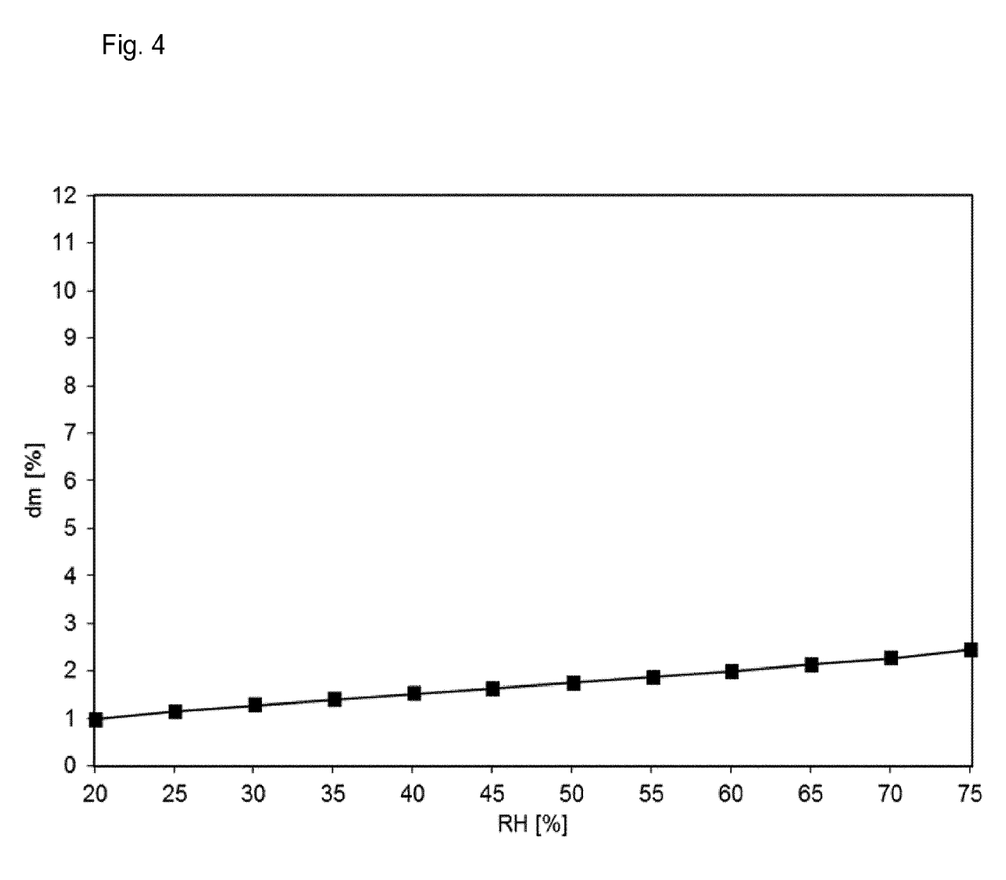
FIG. 4 shows the gravimetric vapour sorption behaviour in the range of 20 to 75% RH at 25° C. (coming from low % RH and going to high % RH, i.e., sorption cycle) of COMPOUND·HCl in the crystalline form 1 as obtained from Example 1A.

34) Another embodiment relates to a crystalline form of COMPOUND·HCl according to any one of embodiments 4) to 7) or 16) to 21), which essentially shows a gravimetric moisture sorption profile (sorption cycle) as depicted in FIG. 4, wherein the gravimetric moisture sorption profile is measured at 25° C.

Figure 5:
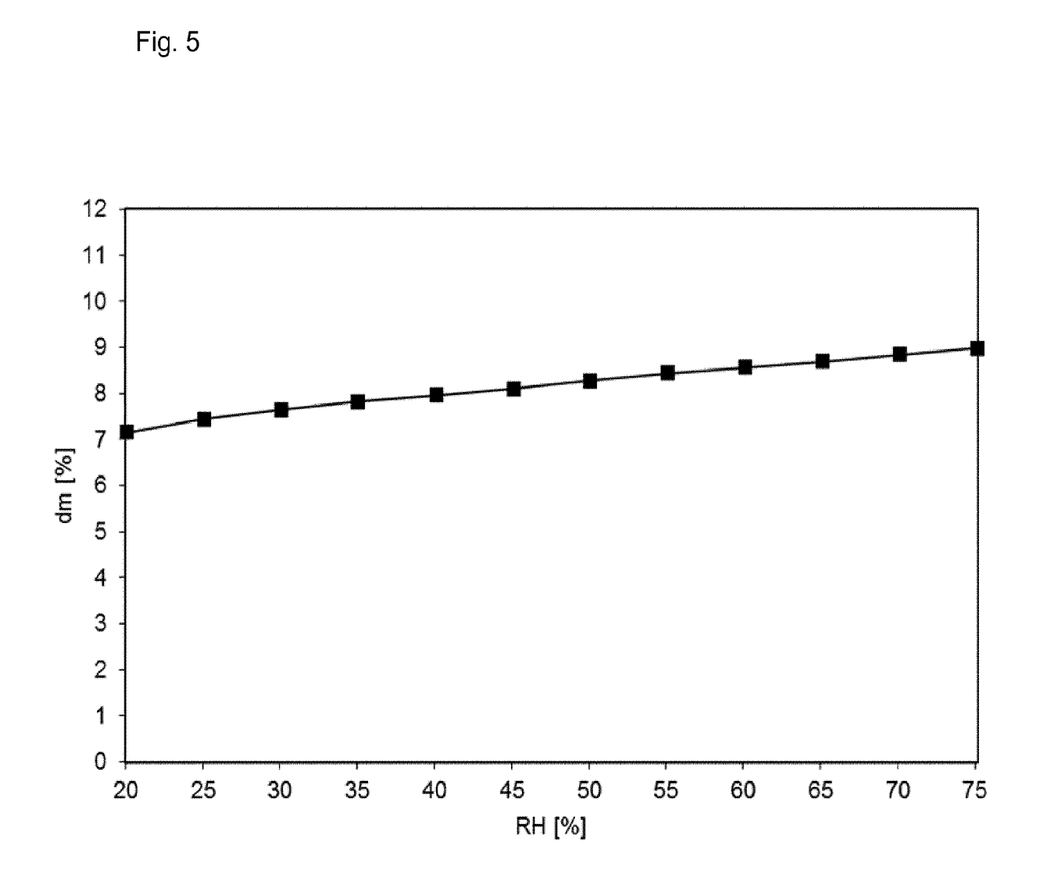
FIG. 5 shows the gravimetric vapour sorption behaviour in the range of 20 to 75% RH at 25° C. (coming from high % RH and going to low % RH, i.e., desorption cycle) of COMPOUND·HCl in the crystalline form 2 as obtained from Example 2.

35) Another embodiment relates to a crystalline form of COMPOUND·HCl according to any one of embodiments 8) to 11) or 22) to 27), which essentially shows a gravimetric moisture sorption profile (desorption cycle) as depicted in FIG. 5, wherein the gravimetric moisture sorption profile is measured at 25° C.

Figure 6:
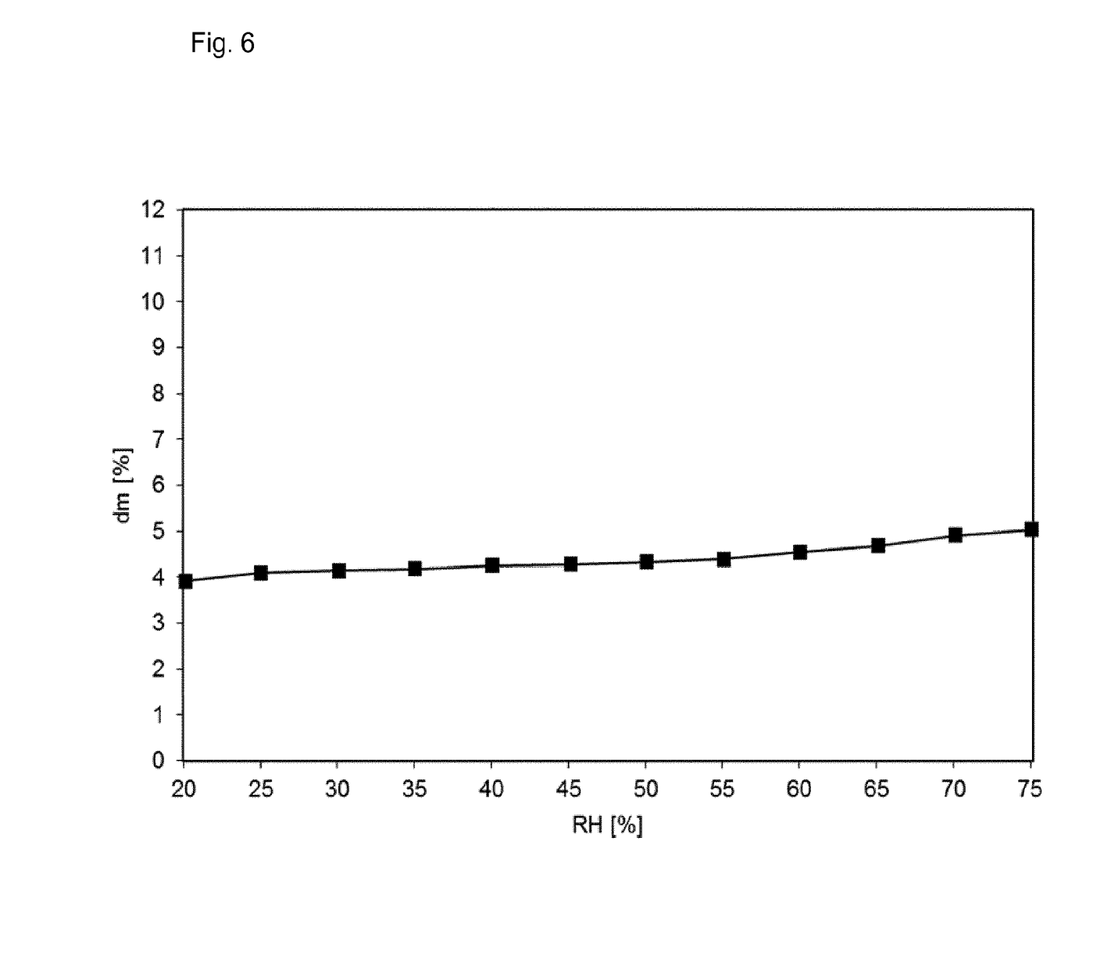
FIG. 6 shows the gravimetric vapour sorption behaviour in the range of 20 to 75% RH at 25° C. (coming from low % RH and going to high % RH, i.e., sorption cycle) of COMPOUND·HCl in the crystalline form 3 as obtained from Example 3A.

36) Another embodiment relates to a crystalline form of COMPOUND·HCl according to any one of embodiments 12) to 15) or 28) to 33), which essentially shows a gravimetric moisture sorption profile (sorption cycle) as depicted in FIG. 6, wherein the gravimetric moisture sorption profile is measured at 25° C.

37) A process for the preparation of COMPOUND·HCl in a crystalline form according to any one of embodiments 1) to 7), wherein the process comprises the following steps:

a. addition of acetone (10 to 30 vol.) to a solution comprising COMPOUND·HCl and a non-polar solvent (0.5 to 3.0 vol.; 0.5 to 3.0 L per kg COMPOUND·HCl) at 45 to 60° C., wherein the non-polar solvent is selected from $(C_{1-12})$chloroalkane;

b. addition of water (0.3 to 0.7 vol.) at 45 to 60° C.;

c. stirring of the mixture under cooling from a temperature of 45 to 60° C. to a temperature at or below 30° C. for at least 1 h; and d. isolation of the obtained crystalline material.

38) A process according to embodiment 37), wherein the amount of added acetone in step a. is about 20 vol.

39) A process according to any one of embodiments 37) or 38), wherein the amount of the non-polar solvent in step a. is 1.0 to 2.0 vol. and wherein the non-polar solvent is dichloromethane.

40) A process according to any one of embodiments 37) to 39), wherein the amount of the added water in step b. is 0.4 to 0.6 vol. (and especially 0.5 vol.).

41) A process according to any one of embodiments 37) to 40), wherein the mixture is stirred in step c. between 1 and 4 h at a temperature of 45 to 60° C. and is subsequently cooled to a temperature between 20 and 30° C. (especially 25° C.) during 1 to 2 h.

42) A process according to any one of embodiments 37) to 41), wherein the isolation in step d. is done by filtration.

43) A process according to any one of embodiments 37) to 42), wherein the solution comprising COMPOUND·HCl and a non-polar solvent used in step a. is obtained by a process comprising the steps:

a. coupling of (S)-6-(3-methoxypyrrolidin-1-yl)-2-phenylpyrimidine-4-carboxylic acid, or a salt thereof (especially a sodium salt thereof), with butyl(R)-4-(2-amino-3-(diethoxyphosphoryl)propanoyl)piperazine-1-carboxylate in the presence of an amide coupling agent;

b. extraction with a solvent mixture comprising $(C_{1-12})$chloroalkane (especially dichloromethane); and water or an aqueous solution of an inorganic salt (especially an aqueous sodium hydrogencarbonat solution)

c. addition of aqueous hydrochloric acid and stirring of the mixture;

d. extraction with a solvent mixture comprising ($C_{1-12}$)chloroalkane (especially dichloromethane); and water or an aqueous solution of an inorganic salt (especially water); and
e. removal of solvents until the amount of ($C_{1-12}$) chloroalkane equals 0.5 to 3.0 L per kg (especially 1.0 to 2.0 L per kg) COMPOUND·HCl.

Based on the dependencies of the different embodiments 1) to 43) as disclosed hereinabove, the following embodiments are thus possible and intended and herewith specifically disclosed in individualised form:

1,2+1, 3+1, 4+1, 5+1, 6+1, 7+1, 8+1, 9+1, 10+1, 11+1, 12+1, 13+1, 14+1, 15+1, 16, 17+16, 18+16, 19+16, 20+16, 21+4+1, 21+5+1, 21+6+1, 21+7+1, 22, 23+22, 24+22, 25+22, 26+22, 27+8+1, 27+9+1, 27+10+1, 27+11+1, 28, 29+28, 30+28, 31+28, 32+28, 33+12+1, 33+13+1, 33+14+1, 33+15+1, 34+4+1, 34+5+1, 34+6+1, 34+7+1, 34+16, 34+17+16, 34+18+16, 34+19+16, 34+20+16, 34+21+4+1, 34+21+5+1, 34+21+6+1, 34+21+7+1, 35+8+1, 35+9+1, 35+10+1, 35+11+1, 35+22, 35+23+22, 35+24+22, 35+25+22, 35+26+22, 35+27+8+1, 35+27+9+1, 35+27+10+1, 35+27+11+1, 36+12+1, 36+13+1, 36+14+1, 36+15+1, 36+28, 36+29+28, 36+30+28, 36+31+28, 36+32+28, 36+33+12+1, 36+33+13+1, 36+33+14+1, 36+33+15+1, 37, 38+37, 39+37, 39+38+37, 40+37, 40+38+37, 40+39+37, 40+39+38+37, 41+37, 41+38+37, 41+39+37, 41+39+38+37, 41+40+37, 41+40+38+37, 41+40+39+37, 41+40+39+38+37, 42+37, 42+38+37, 42+39+37, 42+39+38+37, 42+40+37, 42+40+38+37, 42+40+39+37, 42+40+39+38+37, 42+41+37, 42+41+38+37, 42+41+39+37, 42+41+39+38+37, 42+41+40+37, 42+41+40+38+37, 42+41+40+39+37, 42+41+40+39+38+37, 43+37, 43+38+37, 43+39+37, 43+39+38+37, 43+40+37, 43+40+38+37, 43+40+39+37, 43+40+39+38+37, 43+41+37, 43+41+38+37, 43+41+39+37, 43+41+39+38+37, 43+41+40+37, 43+41+40+38+37, 43+41+40+39+37, 43+41+40+39+38+37, 43+42+37, 43+42+38+37, 43+42+39+37, 43+42+39+38+37, 43+42+40+37, 43+42+40+38+37, 43+42+40+39+37, 43+42+40+39+38+37, 43+42+41+37, 43+42+41+38+37, 43+42+41+39+37, 43+42+41+39+38+37, 43+42+41+40+37, 43+42+41+40+38+37, 43+42+41+40+39+37, 43+42+41+40+39+38+37;

in the list above the numbers refer to the embodiments according to their numbering provided hereinabove whereas "+" indicates the dependency from another embodiment. The different individualised embodiments are separated by commas. In other words, "21+4+1" for example refers to embodiment 21) depending on embodiment 4), depending on embodiment 1), i.e. embodiment "21+4+1" corresponds to embodiment 1) further characterised by the features of the embodiments 4) and 21).

For avoidance of any doubt, whenever one of the above embodiments refers to "peaks in the X-ray powder diffraction diagram at the following angles of refraction 2θ", said X-ray powder diffraction diagram is obtained by using combined Cu Kα1 and Kα2 radiation, without Kα2 stripping; and it should be understood that the accuracy of the 2θ values as provided herein is in the range of +/−0.1-0.2°. Notably, when specifying an angle of refraction 2theta (2θ) for a peak in the invention embodiments and the claims, the 2θ value given is to be understood as an interval from said value minus 0.2° to said value plus 0.2° (2θ+/−0.2°); and preferably from said value minus 0.1° to said value plus 0.1° (2θ+/−0.1°).

Where the plural form is used for compounds, solids, pharmaceutical compositions, diseases and the like, this is intended to mean also a single compound, solid, pharmaceutical composition, disease or the like.

Definitions provided herein are intended to apply uniformly to the subject matter as defined in any one of embodiments 1) to 43), and, mutatis mutandis, throughout the description and the claims unless an otherwise expressly set out definition provides a broader or narrower definition. It is well understood that a definition or preferred definition of a term or expression defines and may replace the respective term or expression independently of (and in combination with) any definition or preferred definition of any or all other terms or expressions as defined herein.

The term "($C_{1-12}$)chloroalkane" refers to an alkane group containing one or two carbon atoms in which one or more (and possibly all) hydrogen atoms have been replaced with chlorine. For example a ($C_{1-12}$)chloroalkane group contains one or two carbon atoms in which one to six (especially two) hydrogen atoms have been replaced with chlorine. Preferred examples of ($C_{1-12}$)chloroalkane groups are dichloromethane and 1,2-dichloroethane (and especially dichloromethane).

The term "amide coupling agent" refers to a compound that promotes the formation of a chemical bond (amide bond) between the —COOH group of a carboxylic acid and the —$NH_2$ group of an amine. Representative examples of amide coupling agents are carbodiimides (such as dicyclohexylcarbodiimide, diisopropylcarbodiimide or 1-ethyl-3-(3-dimethylamino-propyl)carbodiimide) in the presence or absence of an additive such as 1-hydroxy-benzotriazole, 1-hydroxy-7-aza-1H-benzotriazole or N-hydroxysuccinimide; phosphonium reagents (such as benzotriazol-1-yloxy-tris(dimethylamino)-phosphonium hexafluoro-phosphate or benzotriazol-1-yloxy-tripyrrolidino-phosphonium hexafluorophosphate); aminium reagents (such as 2-(1H-benzotriazol-1-yl)-N,N,N',N'-tetramethylaminium tetra-fluoroborate, 2-(1H-benzotriazol-1-yl)-N,N,N',N'-tetramethylaminium hexafluorophosphate or 2-(7-aza-1H-benzotriazol-1-yl)-N,N,N',N'-tetramethylaminium hexafluorophosphate); and 2-propanephosphonic acid anhydride; preferred is 1-ethyl-3-(3-dimethylaminopropyl) carbodiimide in the presence of 1-hydroxy-benzotriazole.

The term "enantiomerically enriched" is understood in the context of the present invention to mean especially that at least 90, preferably at least 95, and most preferably at least 99 percent by weight of the COMPOUND (or of COMPOUND·HCl) are present in form of one enantiomer of the COMPOUND (or of COMPOUND·HCl). It is understood that any reference to "COMPOUND" (or to "COMPOUND·HCl") refers to 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid (or to its HCl salt) in enantiomerically enriched or in pure form.

The term "essentially pure" is understood in the context of the present invention to mean especially that at least 90, preferably at least 95, and most preferably at least 99 percent by weight of the crystals of COMPOUND·HCl are present in a crystalline form according to the present invention.

When defining the presence of peak in e.g. an X-ray powder diffraction diagram, a common approach is to do this in terms of the S/N ratio (S=signal, N=noise). According to this definition, when stating that a peak has to be present in a X-ray powder diffraction diagram, it is understood that the peak in the X-ray powder diffraction diagram is defined by having an S/N ratio (S=signal, N=noise) of greater than x (x being a numerical value greater than 1), usually greater than 2, especially greater than 3.

In the context with stating that the crystalline form essentially shows an X-ray powder diffraction pattern as depicted in FIG. 1, 2, or 3, respectively, the term "essentially" means that at least the major peaks of the diagram depicted in said figures, i.e. those having a relative intensity of more than 20%, especially more than 10%, as compared to the most intense peak in the diagram, have to be present. However, the person skilled in the art of X-ray powder diffraction will recognize that relative intensities in X-ray powder diffraction diagrams may be subject to strong intensity variations due to preferred orientation effects.

The term "equilibration", as used in the context of "equilibration of a sample of COMPOUND·HCl", refers to a process step of keeping a sample for an equilibration time under specific conditions, such as a specifically given relative humidity, a specifically given gas stream and/or a specifically given temperature, wherein the term "equilibration time" refers to the time that is required to obtain an essentially constant content of water in the sample. The content of water is "essentially constant" if the change in the water content is less than 5% if the sample is kept for 24 h under the given specific conditions.

Unless used regarding temperatures, the term "about" placed before a numerical value "X" refers in the current application to an interval extending from X minus 10% of X to X plus 10% of X, and preferably to an interval extending from X minus 5% of X to X plus 5% of X; most preferred is X. In the particular case of temperatures, the term "about" placed before a temperature "Y" refers in the current application to an interval extending from the temperature Y minus 10° C. to Y plus 10° C., preferably to an interval extending from Y minus 3° C. to Y plus 3° C.; most preferred is Y. Room temperature means a temperature of about 25° C.

Whenever the word "between" or "to" is used to describe a numerical range, it is to be understood that the end points of the indicated range are explicitly included in the range. For example: if a temperature range is described to be between 40° C. and 80° C. (or 40° C. to 80° C.), this means that the end points 40° C. and 80° C. are included in the range; or if a variable is defined as being an integer between 1 and 4 (or 1 to 4), this means that the variable is the integer 1, 2, 3, or 4.

It is understood that 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester hydrochloride (or COMPOUND·HCl) refers to a hydrochloride salt of COMPOUND wherein the salt contains about 1 molar equivalent of HCl per molar equivalent of COMPOUND, especially 0.98 to 1.02 molar equivalent of HCl per molar equivalent of COMPOUND and notably 1.00 molar equivalent of HCl per molar equivalent of COMPOUND.

The expression % w/w refers to a percentage by weight compared to the total weight of the composition considered. Likewise, the expression v/v refers to a ratio by volume of the two components considered.

The crystalline forms, especially the essentially pure crystalline forms, of COMPOUND·HCl according to any one of embodiments 1) to 36) can be used as medicaments, e.g. in the form of pharmaceutical compositions for enteral (such especially oral) or parenteral administration (including topical application or inhalation).

44) Another embodiment thus relates to a crystalline form of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester hydrochloride according to any one of embodiments 1) to 36) for use as a medicament.

45) Another embodiment relates to COMPOUND, or a pharmaceutically acceptable salt thereof, for use as a medicament, wherein COMPOUND, or a pharmaceutically acceptable salt thereof, is obtained from a crystalline form of COMPOUND·HCl according to any one of embodiments 1) to 36).

The term "pharmaceutically acceptable salt" refers to a salt that retains the desired biological activity of the subject compound and exhibits minimal undesired toxicological effects. Such salts include inorganic or organic acid and/or base addition salts depending on the presence of basic and/or acidic groups in the subject compound. For reference see for example 'Handbook of Pharmaceutical Salts. Properties, Selection and Use.', P. Heinrich Stahl, Camille G. Wermuth (Eds.), Wiley-VCH, 2008, and 'Pharmaceutical Salts and Co-crystals', Johan Wouters and Luc Quéré (Eds.), RSC Publishing, 2012.

The crystalline solid, especially the essentially pure crystalline solid, of COMPOUND·HCl according to any one of embodiments 1) to 36) may be used as single component or as mixture with other crystalline forms or amorphous form of COMPOUND·HCl.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the crystalline form of the present invention, optionally in combination with other therapeutically valuable substances, into a galenical administration form together with suitable, non-toxic, inert, pharmaceutically acceptable solid or liquid carrier materials and, if desired, usual pharmaceutical adjuvants.

46) A further embodiment of the invention relates to pharmaceutical compositions comprising as active ingredient a crystalline form of COMPOUND·HCl according to any one of embodiments 1) to 36), and at least one pharmaceutically acceptable carrier material.

47) A further embodiment of the invention relates to pharmaceutical compositions comprising as active ingredient COMPOUND, or a pharmaceutically acceptable salt thereof, and at least one pharmaceutically acceptable carrier material, wherein COMPOUND, or a pharmaceutically acceptable salt thereof, is obtained from a crystalline form of COMPOUND·HCl according to any one of embodiments 1) to 36).

48) A further embodiment of the invention relates to a crystalline form of COMPOUND·HCl according to any one of embodiments 1) to 36), for use in the manufacture of a pharmaceutical composition, wherein said pharmaceutical composition comprises as active ingredient the COMPOUND·HCl, and at least one pharmaceutically acceptable carrier material.

49) A further embodiment of the invention relates to COMPOUND, or a pharmaceutically acceptable salt thereof, for use in the manufacture of a pharmaceutical composition, wherein said pharmaceutical composition comprises as active ingredient the COMPOUND, or a pharmaceutically acceptable salt thereof, and at least one pharmaceutically acceptable carrier material, wherein the COMPOUND is obtained from a crystalline form of COMPOUND·HCl according to any one of embodiments 1) to 36).

50) A further embodiment of the invention relates to a crystalline form of COMPOUND·HCl according to any one of embodiments 1) to 36), for use in the prevention/prophylaxis or treatment of diseases selected from the group consisting of acute arterial thrombosis.

51) A preferred embodiment of the invention relates to a crystalline form of COMPOUND·HCl according to any one of embodiments 1) to 36), for use in the prevention/prophylaxis or treatment of diseases selected from the group consisting of acute coronary syndromes, peripheral ischaemia, amaurosis, ischaemic stroke and transient ischaemic attack.

52) A most preferred embodiment of the invention relates to a crystalline form of COMPOUND·HCl according to any one of embodiments 1) to 36), for use in the prevention/prophylaxis or treatment of acute coronary syndromes.

53) A further embodiment of the invention relates to COMPOUND, or a pharmaceutically acceptable salt thereof, for use in the prevention/prophylaxis or treatment of a disease selected from the diseases according to any one of embodiments 50) to 52), wherein the COMPOUND, or a pharmaceutically acceptable salt thereof, is obtained from a crystalline form of COMPOUND·HCl according to any one of embodiments 1) to 36).

54) A further embodiment of the invention relates to a crystalline form of COMPOUND·HCl according to any one of embodiments 1) to 36), for use in the manufacture of a pharmaceutical composition for the prevention/prophylaxis or treatment of diseases selected from the group consisting of acute arterial thrombosis.

55) A preferred embodiment of the invention relates to a crystalline form of COMPOUND·HCl according to any one of embodiments 1) to 36), for use in the manufacture of a pharmaceutical composition for the prevention/prophylaxis or treatment of diseases selected from the group consisting of acute coronary syndromes, peripheral ischaemia, amaurosis, ischaemic stroke and transient ischaemic attack.

56) A most preferred embodiment of the invention relates to a crystalline form of COMPOUND·HCl according to any one of embodiments 1) to 36), for use in the manufacture of a pharmaceutical composition for the prevention/prophylaxis or treatment of acute coronary syndromes.

57) A further embodiment of the invention relates to COMPOUND, or a pharmaceutically acceptable salt thereof, for use in the manufacture of a pharmaceutical composition for the prevention/prophylaxis or treatment of a disease selected from the diseases according to any one of embodiments 54) to 56), wherein the COMPOUND, or a pharmaceutically acceptable salt thereof, is obtained from a crystalline form of COMPOUND·HCl according to any one of embodiments 1) to 36).

58) A further embodiment of the invention relates to pharmaceutical compositions according to embodiment 46), for use in the prevention/prophylaxis or treatment of diseases selected from the group consisting of acute arterial thrombosis.

59) A preferred embodiment of the invention relates to pharmaceutical compositions according to embodiment 46), for use in the prevention/prophylaxis or treatment of diseases selected from the group consisting of acute coronary syndromes, peripheral ischaemia, amaurosis, ischaemic stroke and transient ischaemic attack.

60) A most preferred embodiment of the invention relates to pharmaceutical compositions according to embodiment 46), for use in the prevention/prophylaxis or treatment of acute coronary syndromes.

61) A further embodiment of the invention relates to pharmaceutical compositions according to embodiment 47), for use in the prevention/prophylaxis or treatment of a disease selected from the diseases according to any one of embodiments 58) to 60).

The present invention also relates to a method for the prevention/prophylaxis or treatment of a disease or disorder mentioned herein, comprising administering to a subject a pharmaceutically active amount of a crystalline form of COMPOUND·HCl according to any one of embodiments 1) to 36), or of a pharmaceutical composition according to embodiment 46).

The present invention also relates to a method for the prevention/prophylaxis or treatment of a disease or disorder mentioned herein, comprising administering to a subject a pharmaceutically active amount of the COMPOUND, or a pharmaceutically acceptable salt thereof, wherein the COMPOUND, or a pharmaceutically acceptable salt thereof, is obtained from a crystalline form of COMPOUND·HCl according to any one of embodiments 1) to 36), or of the pharmaceutical composition according to embodiment 47).

Experimental Procedures

Abbreviations (as Used Hereinbefore or Hereinafter)

AP Aqueous layer
aq. Aqueous
Bu Butyl such as in n-Bu=n-butyl
conc. Concentrated
DCM Dichloromethane
EDCl 1-Ethyl-3-(3-dimethylaminopropyl)carbodiimide
eq Equivalent(s)
Et Ethyl
EtOAc Ethyl acetate
EtOH Ethanol
Fig Figure
h Hour(s)
$^1$H-NMR Nuclear magnetic resonance of the proton
HOBt 1-Hydroxy-benzotriazole mono hydrate
HPLC High performance liquid chromatography
IPC In-process control
LC-MS Liquid chromatography-Mass Spectrometry
Me Methyl
MeCN Acetonitrile
MeOH Methanol
mW milli-Watt
min Minute(s)
MS Mass spectrometry
N Normality
NMR Nuclear magnetic resonance
prep. Preparative
RH relative humidity
RT Room temperature
sat. Saturated
sec Second(s)
$T_e$ External temperature
$T_i$ Internal temperature
TFA trifluoroacetic acid THF Tetrahydrofuran
$t_R$ Retention time
UPLC Ultra Performance Liquid Chromatography
UV Ultra violet
vol. L solvent per kg starting material
XRPD X-ray powder diffraction All solvents and reagents are used as obtained from commercial sources unless otherwise indicated.

Temperatures are indicated in degrees Celsius (° C.). Unless otherwise indicated, the reactions take place at room temperature (RT).

In mixtures, relations of parts of solvent or eluent or reagent mixtures in liquid form are given as volume relations (v/v), unless indicated otherwise.

Compounds described in the invention are characterized by UPLC and chiral HPLC (retention time $t_R$ is given in min using the conditions listed below).

Analytical UPLC Conditions as Used in the Examples Below

UPLC Analyses are Performed Using the Following Elution Condition:

Analytical UPLC on YMC Triart ExRS (Part. No. TAR08S03-1003PTH) column (100 mm×3.0 mm, 3 μm); Gradient of 20 mM Ammonium acetate+10 mM $NH_4PF_6$ buffer/Acetonitrile 95/5 (A) and Acetonitrile/Ammonium acetate 10 mM (B) from 8% to 100% B over 19 min; flow rate 0.5 ml/min, detection at 210 nm.

Analytical HPLC over a chiral stationary phase are performed on a Chiralpak A D-H (4.6×250 mm, 5 μm) column. Typical conditions of chiral HPLC are an isocratic mixture of Hexane/Ethanol/TFA (80:20:0.1 v/v/v), at a flow rate of 0.8 mL/min., at 40° C.; detection at 247 nm.

X-Ray Powder Diffraction Analysis (XRPD)

X-ray powder diffraction patterns were collected on a Bruker D8 Advance X-ray diffractometer equipped with a Lynxeye detector operated with CuKα-radiation in reflection mode (coupled two Theta/Theta). Typically, the X-ray tube was run at of 40 kV/40 mA. A step size of 0.02° (2θ) and a step time of 76.8 sec over a scanning range of 3-500 in 2θ were applied. The divergence slits were set to fixed 0.3°. Powders were slightly pressed into a silicon single crystal sample holder with depth of 0.5 mm and samples were rotated in their own plane during the measurement. Diffraction data are reported without application of Kα2 stripping. The accuracy of the 2θ values as provided herein is in the range of +/−0.1-0.2° as it is generally the case for conventionally recorded X-ray powder diffraction patterns.

Gravimetric Vapour Sorption (GVS) Analysis

Measurements were performed on an IGASORP Model HAS-036-080 moisture sorption instrument (Hiden Isochema, Warrington, UK) operated in stepping mode at 25° C. The sample was allowed to equilibrate at the starting relative humidity (RH) before starting a pre-defined humidity program in steps of 5% ARH and with a maximal equilibration time of 24 hours per step. About 20 to 30 mg of each sample was used.

I-Chemistry (S)-6-(3-methoxypyrrolidin-1-yl)-2-phenylpyrimidine-4-carboxylic acid, butyl(R)-4-(2-amino-3-(diethoxyphosphoryl)propanoyl)piperazine-1-carboxylate and 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester (COMPOUND) can be prepared according to the procedures given in WO 2009/069100 (example 2) or Caroff E et al., *J. Med. Chem.* 2015; 58:9133-9153. (S)-6-(3-methoxypyrrolidin-1-yl)-2-phenylpyrimidine-4-carboxylic acid can be transferred into sodium (S)-6-(3-methoxypyrrolidin-1-yl)-2-phenylpyrimidine-4-carboxylate in presence of aqueous sodium hydroxide.

II. Preparation of Crystalline Forms of COMPOUND·HCl

Example 1A: Preparation and Characterization of COMPOUND·HCl in Crystalline Form 1

A 15 L reactor was charged with sodium (S)-6-(3-methoxypyrrolidin-1-yl)-2-phenylpyrimidine-4-carboxylate (584 g, 1.82 mol) and 1-hydroxy-benzotriazole mono hydrate (HOBt) (274 g, 1.1 eq.). Water (1305 mL, 2.0 vol.) was added. The pH of the suspension was 5-6. Butyl(R)-4-(2-amino-3-(diethoxyphosphoryl)propanoyl)piperazine-1-carboxylate (665.7 g, 1.0 eq) was dissolved in tetrahydrofurane (THF) (1960 ml, 3.0 vol.). The solution was added to the reaction at 20 to 30° C. during 5 to 10 min. A solution of 1-ethyl-3-(3-dimethylaminopropyl)carbodiimide (EDCl) (389 g, 1.2 eq.) in water (1305 ml, 2.0 vol.) was added to the reaction at 20 to 30° C. during 15 to 30 min. The pH of the reaction stayed between 6-7. The reaction was stirred during 4 h at 20 to 30° C. An IPC showed 93% conversion. The reaction was diluted with dichloromethane (DCM) (3265 ml, 5.0 vol.) and % sat. aq. sodium hydrogencarbonat solution (3265 ml, 5.0 vol.). The layers were separated. The organic layer was washed again with % sat. aq. sodium hydrogencarbonat solution (3265 ml, 5.0 vol.). The layers were separated. An IPC showed the complete removal of HOBt. The organic layer was washed with aq. 10% citric acid (3265 ml, 5.0 vol.). In total 3.75 L of solvents were distilled off at minimal 800 mbar and $T_e$=75 to 80° C. during 40 min. The residual solution was cooled to 20 to 30° C. Aq. 32% HCl (3 L, 19 eq.) was added during 5 to 10 min at 20 to 30° C. An IPC after 4 h of stirring showed complete hydrolysis. Water (5.2 L, 8 vol.) was added at 20 to 30° C. The reaction was diluted with DCM (5.2 L, 8 vol.). The layers were separated. The aqueous layer was extracted again 2× with DCM (2×5.2 L, 8 vol.). All DCM layers were combined and filtered through a polycap 75 HD filter. In total 14 L of solvents were distilled off during 2 h at atmospheric pressure and $T_e$=75 to 80° C. Acetone (21.6 L, 33 vol.) was added to the refluxing reaction mixture at $T_e$=70 to 75° C. To the refluxing fine suspension water (325 mL, 0.5 vol.) was added. The fine, pale suspension was stirred at reflux during 1.5 h and a thick white slurry was obtained. The slurry was cooled to $T_i$=25° C. during 1 h (ramp). The solid product was isolated by filtration. The filter cake was rinsed with acetone (4.5 L, 7 vol.) and was dried by blowing nitrogen through it to give 750 g (69%) of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester hydrochloride as a white solid.

TABLE 1

Characterisation data for COMPOUND•HCl in crystalline form 1

| Technique | Data Summary | Remarks |
|---|---|---|
| XRPD | Crystalline | see FIG. 1 |
| 1H-NMR | Consistent | |
| Elemental analysis | Corresponds | |
| Purity (UPLC, Area %) | 98.6% | |
| Moisture sorption at 25° C. | Profile measured from low RH to high RH | see FIG. 4 |

Example 1B: Preparation and Characterization of COMPOUND·HCl in Crystalline Form 1

An enameled reactor was charged with water (10.5 L; 1.6 vol.), sodium (S)-6-(3-methoxypyrrolidin-1-yl)-2-phenylpyrimidine-4-carboxylate (6.06 kg; 18.87 mol, 1.12 eq) and 1-hydroxy-benzotriazole mono hydrate (HOBt) (2.71 kg; 17.70 mol; 1.08 eq.). The resulting white suspension was stirred during 60 min at 21° C. A yellow solution of butyl (R)-4-(2-amino-3-(diethoxyphosphoryl)propanoyl)piperazine-1-carboxylate (6.47 kg, 16.45 mol, 1.0 eq.) in THF (41 kg, 46.6 L, 7.2 vol.) was transferred into a stirring tank via inline filter. After addition of this solution into the reactor within 12 min at 20° C. a solution of 1-ethyl-3-(3-dimethylaminopropyl)carbodiimide (EDCl) (4.00 kg; 20.8 mol; 1.26 eq.) in water (13.5 L; 2.1 vol.) was added within 13 min at 20° C. The reaction was stirred during 64 h at 20° C. At 20° C. aq. 3.7% NaHCO$_3$ (32 L; 5.0 vol.) was added into the reactor followed by dichloromethane (DCM) (32 L; 5.0 vol.). The mixture was stirred during 10 min at 20° C. After layer separation the pH of the aqueous layer (AP) was 8-9. The AP was extracted again with DCM (16 L; 2.5 vol.). The combined organic layers were charged into the reactor (total volume=94 L) and were washed with aq. 3.7% NaHCO$_3$ (32 L; 5.0 vol.). After layer separation the pH was 10. The resulting organic layer was washed with aq. 10% citric acid (32 L; 5.0 vol.). The yellow solution was concentrated to a final volume of 5.5 vol. of butyl 4-((R)-3-(diethoxyphosphoryl)-2-(6-((S)-3-methoxypyrrolidin-1-yl)-2-phenylpyrimidine-4-carboxamido)propanoyl)piperazine-1-carboxylate at 55° C. and not below a pressure of 585 mbar. 52 L solvent were removed within 5 h.

The concentrated organic solution was treated with aq. 33% HCl (33 L; 5.1 vol.). The reaction mixture was stirred during 12 h at 20 to 30° C. An IPC showed complete conversion into free phosphonate. At 20 to 30° C. water (53 L; 8.2 vol.) was added into the reactor followed by DCM (53 L; 8.2 vol.). The layers were separated. The aqueous layer was extracted 2× with DCM (53 L; 8.2 vol.). The organic layers were combined and concentrated at T$_j$=50° C. and a pressure not below 900 mbar. 76 L of solvents were removed. Acetone (56 L; 8.7 vol.) was added without interrupting the distillation. The distillation was continued at T$_j$=50° C. until a final amount of 7 vol. remained. The pressure was not below 500 mbar. The concentrated solution was diluted with acetone (120 L; 18.5 vol.). The concentrated solution was stirred at T$_j$=50° C. A white suspension was formed. Within 30 minutes the white suspension was diluted with water (3.4 L; 0.5 vol.) and was stirred during 3.5 h at T$_j$=56° C. The suspension was cooled to 20 to 30° C. within 2 h and stirred at this temperature for 1.5 h. The thick, white suspension was filtered off. The filter cake was washed twice with acetone (2×24 L; 3.7 vol.) and was dried on the filter to give 7.67 kg of ((R)-3-(4-(butoxycarbonyl)piperazin-1-yl)-2-(6-((S)-3-methoxypyrrolidin-1-yl)-2-phenylpyrimidine-4-carboxamido)-3-oxopropyl)phosphonic acid hydrochloride.

TABLE 2

Characterisation data for COMPOUND•HCl in crystalline form 1

| Technique | Data Summary | Remarks |
|---|---|---|
| XRPD | Crystalline | corresponds to FIG. 1 |
| 1H-NMR | Consistent | |
| Purity (UPLC, Area %) | 99.8% | |
| Moisture sorption at 25° C. | Profile measured from low RH to high RH | corresponds to FIG. 4 |

Example 2: Preparation and Characterization of COMPOUND·HCl in Crystalline Form 2

COMPOUND·HCl in crystalline form 1 (100 mg), as obtained by the process described in example 1A, was allowed to equilibrate at a relative humidity of >90% and room temperature for 3 days. The sample was then allowed to equilibrate at 40% RH and room temperature for 1 day to give COMPOUND·HCl in crystalline form 2.

TABLE 3

Characterisation data for COMPOUND•HCl in crystalline form 2

| Technique | Data Summary | Remarks |
|---|---|---|
| XRPD | Crystalline | see FIG. 2 |
| 1H-NMR | Consistent | |
| Moisture sorption at 25° C. | Profile measured from high RH to low RH | see FIG. 5 |

Example 3A: Preparation and Characterization of COMPOUND·HCl in Crystalline Form 3

COMPOUND·HCl in crystalline form 2 (100 mg), as obtained by the process described in example 2, was allowed to equilibrate in a dry nitrogen gas stream (400 mL/min) at room temperature for 1 day. The sample was then allowed to equilibrate at 40% RH and room temperature for 1 day to give COMPOUND·HCl in crystalline form 3.

TABLE 4

Characterisation data for COMPOUND•HCl in crystalline form 3

| Technique | Data Summary | Remarks |
|---|---|---|
| XRPD | Crystalline | see FIG. 3 |
| Moisture sorption at 25° C. | Profile measured from low RH to high RH | see FIG. 6 |

Example 3B: Preparation and Characterization of COMPOUND·HCl in Crystalline Form 3 by Re-Crystallization An enameled reactor was rinsed with acetone (20 L). 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester hydrochloride (1.70 kg), water (1.28 L, 0.75 vol.) and acetone (8.5 L, 5 vol.) were charged and the mixture was heated to T$_j$=40° C. for 34 min.

Additional acetone (17 L, 10 vol.) was added over 47 min. The mixture was further stirred for 37 min at $T_i=40°$ C. and cooled to $T_i=20°$ C. over 67 min. After 2 h at $T_i=20°$ C. the suspension was slowly filtered over 2 h and the crystalline solid was washed twice with acetone (2×10 L, 5.9 vol.). Prolonged drying on the suction filter gave COMPOUND·HCl in crystalline form 3.

TABLE 5

Characterisation data for COMPOUND•HCl in crystalline form 3

| Technique | Data Summary | Remarks |
|---|---|---|
| XRPD | Crystalline | corresponds to FIG. 3 |
| 1H-NMR | Consistent | |

The invention claimed is:

1. A method for the treatment of a disease that is responsive to the inhibition of platelet aggregation, the method comprising administering to a subject in need thereof a pharmaceutical composition comprising as active ingredient a $P2Y_{12}$ receptor antagonist which is 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester, or a pharmaceutically acceptable salt thereof, and at least one pharmaceutically acceptable carrier material, wherein 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester, or the pharmaceutically acceptable salt thereof, is obtained from a crystalline form of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester hydrochloride, wherein the crystalline form of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester hydrochloride is characterized by:
    a. the presence of peaks in the X-ray powder diffraction diagram at the following angles of refraction 2θ: 4.0°, 5.0°, and 15.3°; or
    b. the presence of peaks in the X-ray powder diffraction diagram at the following angles of refraction 2θ: 5.2°, 6.8°, and 10.3°; or
    c. the presence of peaks in the X-ray powder diffraction diagram at the following angles of refraction 2θ: 5.5°, 11.0°, and 16.6°.

2. The method according to claim 1, wherein the crystalline form of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester hydrochloride is characterized by:
    a. the presence of peaks in the X-ray powder diffraction diagram at the following angles of refraction 2θ: 4.0°, 5.0°, 11.7°, 15.3°, and 19.3°; or
    b. the presence of peaks in the X-ray powder diffraction diagram at the following angles of refraction 2θ: 5.2°, 6.8°, 10.3°, 10.8°, and 15.4°; or
    c. the presence of peaks in the X-ray powder diffraction diagram at the following angles of refraction 2θ: 5.5°, 7.2°, 11.0°, 11.5°, and 16.6°.

3. The method according to claim 1, wherein the crystalline form of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester hydrochloride is characterized by:
    a. the presence of peaks in the X-ray powder diffraction diagram at the following angles of refraction 2θ: 4.0°, 5.0°, 5.9°, 11.7°, 15.3°, 16.9°, 19.3°, 19.7°, and 20.7°; or
    b. the presence of peaks in the X-ray powder diffraction diagram at the following angles of refraction 2θ: 5.2°, 6.8°, 8.0°, 10.3°, 10.8°, 12.7°, 15.4°, 16.2°, 20.3°, and 21.7°; or
    c. the presence of peaks in the X-ray powder diffraction diagram at the following angles of refraction 2θ: 5.5°, 7.2°, 11.0°, 11.5°, 14.4°, 16.6°, 18.1°, 21.1°, and 22.0°.

4. The method according to claim 1, wherein the crystalline form of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester hydrochloride is characterized by the presence of peaks in the X-ray powder diffraction diagram at the following angles of refraction 2θ: 4.0°, 5.0°, 11.7°, 15.3°, and 19.3°.

5. The method according to claim 1, wherein the crystalline form of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester hydrochloride is characterized by the presence of peaks in the X-ray powder diffraction diagram at the following angles of refraction 2θ: 5.2°, 6.8°, 10.3°, 10.8°, and 15.4°.

6. The method according to claim 1, wherein the crystalline form of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester hydrochloride is characterized by the presence of peaks in the X-ray powder diffraction diagram at the following angles of refraction 2θ: 4.0°, 5.0°, 5.9°, 11.7°, 15.3°, 16.9°, 19.3°, 19.7°, and 20.7°.

7. The method according to claim 1, wherein the crystalline form of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester hydrochloride is characterized by the presence of peaks in the X-ray powder diffraction diagram at the following angles of refraction 2θ: 5.2°, 6.8°, 8.0°, 10.3°, 10.8°, 12.7°, 15.4°, 16.2°, 20.3°, and 21.7°.

8. The method according to claim 1, wherein the at least one pharmaceutically acceptable carrier material is a pharmaceutically acceptable liquid carrier material.

9. The method according to claim 2, wherein the at least one pharmaceutically acceptable carrier material is a pharmaceutically acceptable liquid carrier material.

10. The method according to claim 3, wherein the at least one pharmaceutically acceptable carrier material is a pharmaceutically acceptable liquid carrier material.

11. The method according to claim 4, wherein the at least one pharmaceutically acceptable carrier material is a pharmaceutically acceptable liquid carrier material.

12. The method according to claim 5, wherein the at least one pharmaceutically acceptable carrier material is a pharmaceutically acceptable liquid carrier material.

13. The method according to claim 6, wherein the at least one pharmaceutically acceptable carrier material is a pharmaceutically acceptable liquid carrier material.

14. The method according to claim 7, wherein the at least one pharmaceutically acceptable carrier material is a pharmaceutically acceptable liquid carrier material.

* * * * *